(12) United States Patent
Anderson et al.

(10) Patent No.: US 7,658,709 B2
(45) Date of Patent: *Feb. 9, 2010

(54) SHAPE MEMORY ALLOY ACTUATORS

(75) Inventors: David A. Anderson, Andover, MN (US); James F. Kelley, Coon Rapids, MN (US); Naim S. Istephanous, Roseville, MN (US); Steven L. Waldhauser, Circle Pines, MN (US)

(73) Assignee: Medtronic, Inc., Minneaoplis, MN (US)

( * ) Notice: Subject to any disclaimer, the term of this patent is extended or adjusted under 35 U.S.C. 154(b) by 658 days.

This patent is subject to a terminal disclaimer.

(21) Appl. No.: 10/410,546

(22) Filed: Apr. 9, 2003

(65) Prior Publication Data

US 2004/0204676 A1 Oct. 14, 2004

(51) Int. Cl.
*A61B 1/00* (2006.01)

(52) U.S. Cl. .................. 600/143; 600/151; 60/527; 60/528; 604/95.05

(58) Field of Classification Search ............ 600/143, 600/151; 604/95.04, 95.05; 606/78; 623/1.18; 60/527–529
See application file for complete search history.

(56) References Cited

U.S. PATENT DOCUMENTS

| | | | | | |
|---|---|---|---|---|---|
| 3,615,913 | A | * | 10/1971 | Shaw | 148/33.3 |
| 4,543,090 | A | | 9/1985 | McCoy | 604/95 |
| 4,551,974 | A | * | 11/1985 | Yaeger et al. | 60/527 |
| 4,765,139 | A | | 8/1988 | Wood | 60/527 |
| 4,790,624 | A | | 12/1988 | Van Hoye et al. | 350/96.26 OC |
| 4,944,727 | A | * | 7/1990 | McCoy | 604/528 |
| 5,061,914 | A | * | 10/1991 | Busch et al. | 337/140 |
| 5,298,114 | A | * | 3/1994 | Takeshita | 216/13 |
| 5,335,498 | A | | 8/1994 | Komatsu et al. | 60/528 |
| 5,405,337 | A | * | 4/1995 | Maynard | 604/531 |
| 5,410,290 | A | * | 4/1995 | Cho | 337/140 |
| 5,597,378 | A | * | 1/1997 | Jervis | 606/78 |
| 5,619,177 | A | * | 4/1997 | Johnson et al. | 337/140 |
| 5,763,979 | A | | 6/1998 | Mukherjee et al. | 310/306 |
| 5,800,500 | A | * | 9/1998 | Spelman et al. | 607/137 |
| 5,804,276 | A | | 9/1998 | Jacobs et al. | 428/110 |
| 5,941,249 | A | * | 8/1999 | Maynard | 128/898 |
| 6,021,355 | A | * | 2/2000 | Shchervinsky | 607/132 |
| 6,072,154 | A | | 6/2000 | Maynard | 219/209 |
| 6,103,033 | A | * | 8/2000 | Say et al. | 156/73.1 |
| 6,133,547 | A | | 10/2000 | Maynard | 219/209 |
| 6,245,092 | B1 | * | 6/2001 | Schaldach, Jr. | 607/1 |

(Continued)

FOREIGN PATENT DOCUMENTS

EP  1 010 440  6/2000

(Continued)

*Primary Examiner*—Max Hindenburg
*Assistant Examiner*—Rene Towa
(74) *Attorney, Agent, or Firm*—Carol F. Barry

(57) ABSTRACT

A shape memory alloy (SMA) actuator includes a groove formed in a surface of a shape memory alloy (SMA) substrate establishing a trace pattern for a layer of conductive material formed over an electrically insulative layer. The trace pattern includes a first end, a second end, and a heating element disposed between the first and second ends. The SMA substrate is trained to deform at a transition temperature achieved when electricity is conducted through the conductive material via first and second interconnect pads terminating the first and second ends of the trace pattern.

28 Claims, 7 Drawing Sheets

U.S. PATENT DOCUMENTS

| | | | |
|---|---|---|---|
| 6,323,459 B1 | 11/2001 | Maynard | 219/209 |
| 6,326,707 B1 * | 12/2001 | Gummin et al. | 310/12 |
| 6,422,011 B1 * | 7/2002 | Sinclair | 60/528 |
| 6,447,478 B1 | 9/2002 | Maynard | 604/95.05 |
| 6,464,200 B1 * | 10/2002 | Hines et al. | 251/11 |
| 6,612,110 B1 * | 9/2003 | Silverbrook | 60/528 |
| 6,832,478 B2 * | 12/2004 | Anderson et al. | 60/527 |
| 6,917,276 B1 * | 7/2005 | Menard et al. | 337/140 |
| 2001/0039449 A1 * | 11/2001 | Johnson et al. | 623/1.19 |
| 2003/0010923 A1 * | 1/2003 | Zur | 250/370.09 |

FOREIGN PATENT DOCUMENTS

| | | |
|---|---|---|
| WO | WO 94/19051 | 1/1994 |
| WO | WO 03/089040 A1 | 10/2003 |

* cited by examiner

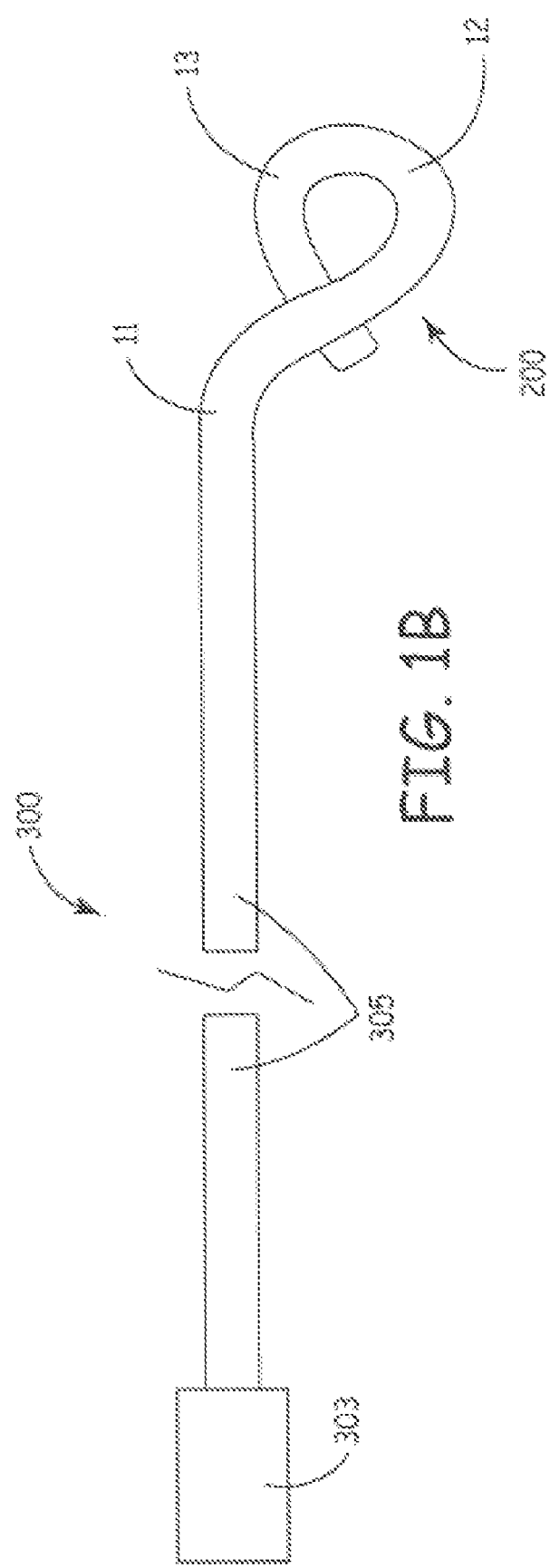

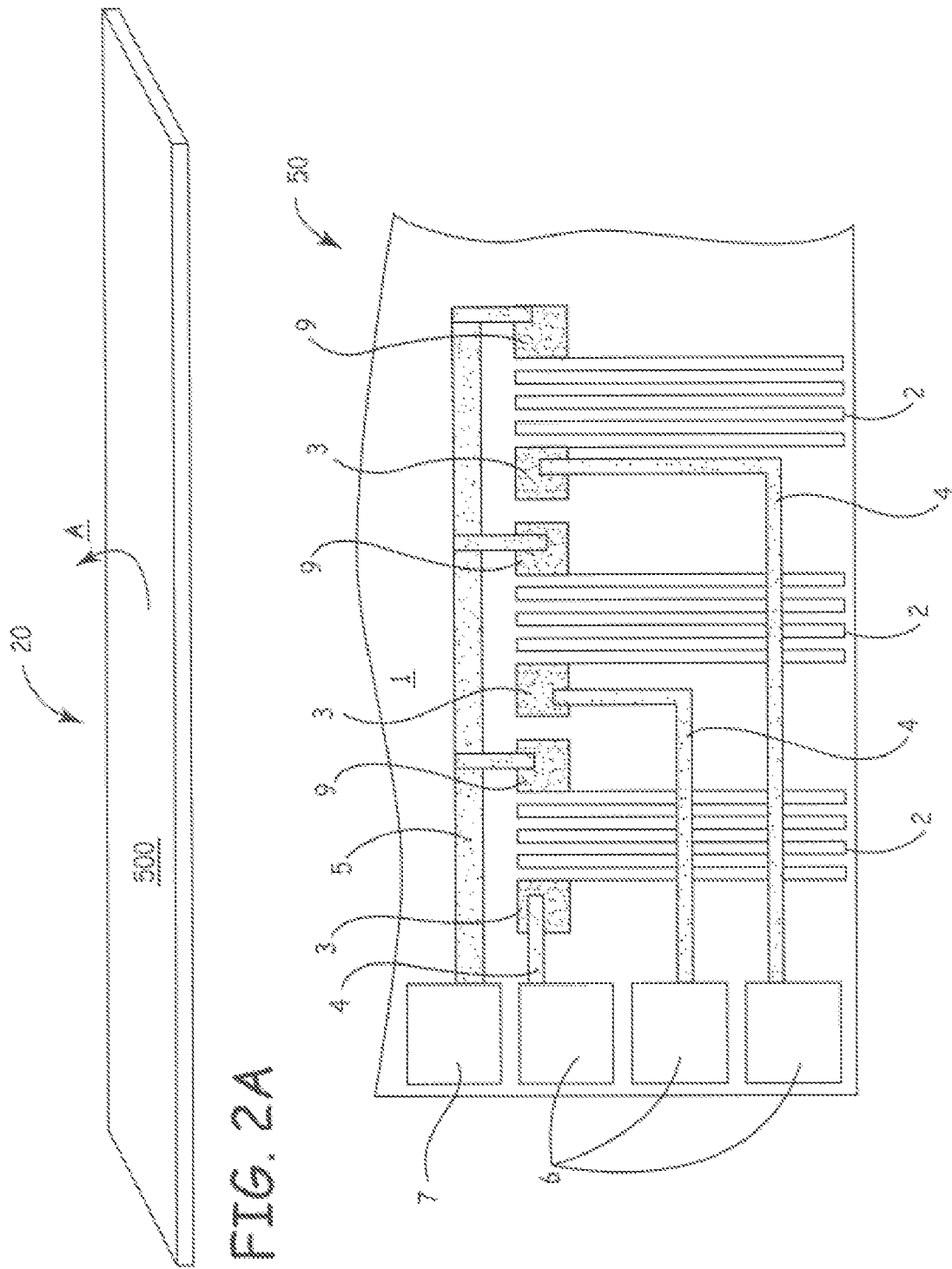

SHAPE MEMORY ALLOY ACTUATORS

CROSS-REFERENCE TO RELATED APPLICATION

Cross-reference is hereby made to commonly-assigned related U.S. Pat. No. 6,832,478, issued on Dec. 21, 2004, to David Anderson, et al., entitled "Shape Memory Alloy Actuators".

FIELD OF THE INVENTION

Embodiments of the present invention relate generally to shape memory alloy (SMA) actuators and more particularly to means for forming SMA actuators and incorporating such actuators into elongated medical devices.

BACKGROUND

The term SMA is applied to a group of metallic materials which, when subjected to appropriate thermal loading, are able to return to a previously defined shape or size. Generally an SMA material may be plastically deformed at some relatively low temperature and will return to a pre-deformation shape upon exposure to some higher temperature by means of a micro-structural transformation from a flexible martensitic phase at the low temperature to an austenitic phase at a higher temperature. The temperature at which the transformation takes place is known as the activation temperature. In one example, a TiNi alloy has an activation temperature of approximately 70° C. An SMA is "trained" into a particular shape by heating it well beyond its activation temperature to its annealing temperature where it is held for a period of time. In one example, a TiNi alloy is constrained in a desired shape and then heated to 510° C. and held at that temperature for approximately fifteen minutes.

In the field of medical devices SMA materials, for example TiNi alloys, such as Nitinol, or Cu alloys, may form a basis for actuators designed to impart controlled deformation to elongated interventional devices. Examples of these devices include delivery catheters, guide wires, electrophysiology catheters, ablation catheters, and electrical leads, all of which require a degree of steering to access target sites within a body; that steering is facilitated by an SMA actuator. An SMA actuator within an interventional device typically includes a strip of SMA material extending along a portion of a length of the device and one or more resistive heating elements through which electrical current is directed. Each heating element is attached to a surface of the SMA strip, in proximity to portions of the SMA strip that have been trained to bend upon application of thermal loading. A layer of electrically insulating material is disposed over a portion of the SMA strip on which a conductive material is deposited or applied in a trace pattern forming the heating element. Electrical current is directed through the conductive trace from wires attached to interconnect pads that terminate each end of the trace. In this way, the SMA material is heat activated while insulated from the electrical current. It is important that, during many cycles of activation, the insulative layer does not crack or delaminate from the surface of the SMA strip.

BRIEF DESCRIPTION OF THE DRAWINGS

FIG. 1B is a plan view of the exemplary device of FIG. 1A wherein a current has been passed through heating elements of the SMA actuator.

FIG. 2A is a perspective view of an SMA substrate or strip that would be incorporated in an SMA actuator.

FIG. 2B is a plan view of a portion of a surface of an SMA actuator.

DETAILED DESCRIPTION

Figure 1A:
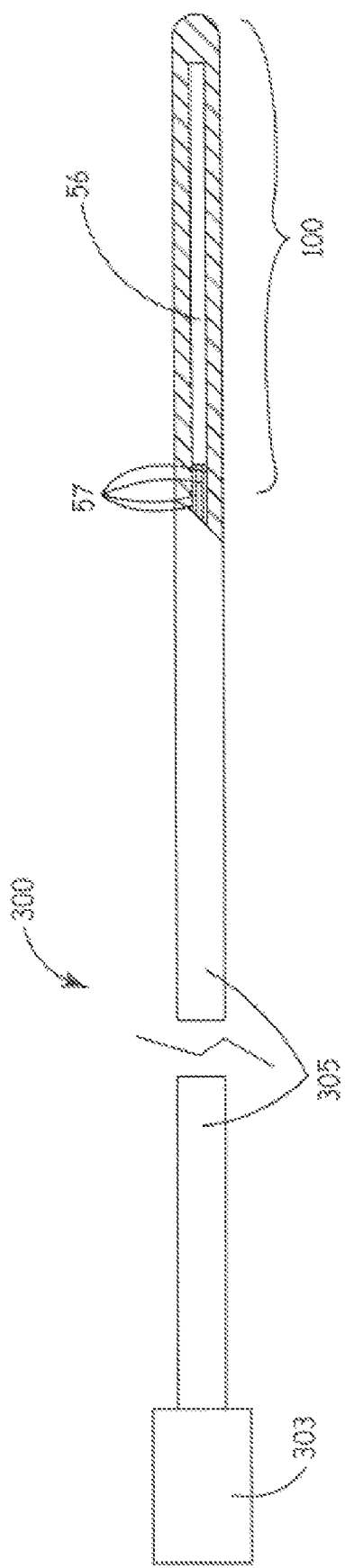
FIG. 1A is a plan view including a partial section of an elongated medical device including an SMA actuator.

FIGS. 1A-D illustrate two examples of elongated medical devices each incorporating an SMA actuator, wherein each actuator serves to control deformation of a portion of each device. FIG. 1A is a plan view with partial section of an elongated medical device 300 including an SMA actuator 56. As illustrated in FIG. 1A, medical device 300 further includes a shaft 305, a hub 303 terminating a proximal end of shaft 305, and conductor wires 57 coupled to SMA actuator 56. SMA actuator 56, positioned within a distal portion 100 of shaft 305, includes a plurality of heating elements (not shown), electrically insulated from an SMA substrate, through which current flows fed by wires 57; wires 57, extending proximally and joined to electrical contacts (not shown) on hub 303, carry current to heat portions of the SMA substrate to an activation temperature. At the activation temperature, portions of the SMA substrate revert to a trained shape, for example a shape 200 as illustrated in FIG. 1B. FIG. 1B is a plan view of the exemplary device 300 of FIG. 1A wherein a current has been passed through heating elements of SMA actuator 56, locations of which heating elements correspond to bends 11, 12, and 13. When the current is cut, either an external force or a spring element (not shown) joined to shaft 605 in proximity of SMA actuator 56 returns distal portion 100 back to a substantially straight form as illustrated in FIG. 1A. Device 300, positioned within a lumen of another elongated medical device, may be used to steer or guide a distal portion of the other device via controlled deformation of actuator 56 at locations corresponding to bends 11, 12, and 13, either all together, as illustrated in FIG. 1B, or individually, or in paired combinations.

Figure 1C:
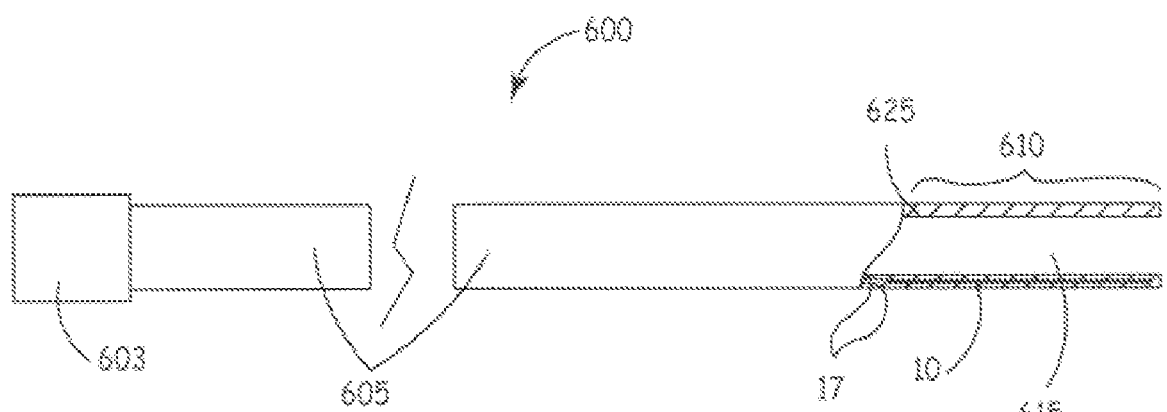
FIG. 1C is a plan view including a partial section of another embodiment of an elongated medical device including an SMA actuator.
Figure 1D:
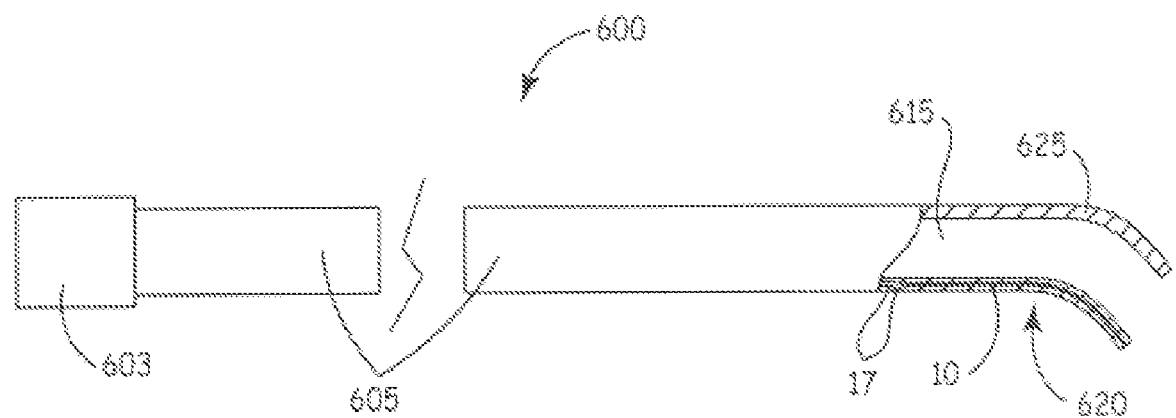
FIG. 1D is a plan view of the exemplary device of FIG. 1C wherein a current has been passed through heating elements of the SMA actuator.

FIG. 1C is a plan view including a partial section of another embodiment of an elongated medical device 600 including an SMA actuator 10 embedded in a portion of a wall 625 of a shaft 605. As illustrated in FIG. 1C, medical device 600 further includes a hub 603 terminating a proximal end of shaft 605, a lumen 615 extending along shaft 605, from a distal portion 610 through hub 603, and conductor wires 17 coupled to SMA actuator 10. SMA actuator 10, positioned within distal portion 610 of shaft 605, includes a plurality of heating elements (not shown), electrically insulated from an SMA substrate, through which current flows fed by wires 17; wires 17, extending proximally and joined to electrical contacts (not shown) on hub 603, carry current to heat portions of the SMA substrate to an activation temperature. At the activation temperature, portions of the SMA substrate revert to a trained shape, for example a bend 620 as illustrated in FIG. 1D. FIG.

1D is a plan view of the exemplary device 600 of FIG. 1C wherein a current has been passed through a heating element of SMA actuator 10, a location of which heating element corresponds to bend 620. When the current is cut, either an external force or a spring element (not shown), for example embedded in a portion of shaft wall 625, returns distal portion 610 back to a substantially straight form as illustrated in FIG. 1C. Lumen 615 of device 600, may form a pathway to slideably engage another elongated medical device, guiding the other device via controlled deformation of distal portion 610 by actuator 10 resulting in bend 620.

FIGS. 2A-B illustrate portions of exemplary SMA actuators that may be incorporated into an elongated medical device, for example device 300 illustrated in FIGS. 1A-B. FIG. 2A is a perspective view of an SMA substrate or strip 20 that would be incorporated into an SMA actuator, such as SMA actuator 56 illustrated in FIG. 1A. Embodiments of the present invention include an SMA substrate, such as strip 20, having a thickness between approximately 0.001 inch and approximately 0.1 inch; a width and a length of strip 20 depends upon construction and functional requirements of a medical device into which strip 20 is integrated. As illustrated in FIG. 2A strip 20 includes a surface 500, which according to embodiments of the present invention includes a layer of an inorganic electrically insulative material formed or deposited directly thereon, examples of which include oxides such as silicon oxide, titanium oxide, or aluminum oxide, nitrides such as boron nitride, silicon nitride, titanium nitride, or aluminum nitride, and carbides such as silicon carbide, titanium carbide, or aluminum carbide. Means for forming the inorganic material layer are well know to those skilled the art and include vacuum deposition methods, such as sputtering, evaporative metalization, plasma assisted vapor deposition, or chemical vapor deposition; other methods include precipitation coating and printing followed by sintering. In an alternate embodiment an SMA substrate, such as strip 20, is a TiNi alloy and a native oxide of the TiNi alloy forms the layer of inorganic electrically insulative material; the native oxide may be chemically, electrochemically or thermally formed on surface 500. In yet another embodiment, a deposited non-native oxide, nitride, or carbide, such as one selected from those mentioned above, in combination with a native oxide forms the layer of electrically insulative material on surface 500.

According to embodiments of the present invention, an SMA substrate, such as strip 20, is trained to bend, for example in the direction indicated by arrow A in FIG. 2A, after deposition or formation of an inorganic electrically insulative layer upon surface 500, since the inorganic insulative layer will not break down under training temperatures. Training temperatures for TiNi alloys range between approximately 300° C. and approximately 800° C. Alternately an SMA substrate, such as strip 20, may be trained to bend before deposition or formation of the inorganic insulative layer if a temperature of the substrate, during a deposition or formation process, is maintained below an activation temperature of the substrate. Furthermore, according to an alternate embodiment, an additional layer of an organic material is deposited over the inorganic layer to form a composite electrically insulative layer. Examples of suitable organic materials include polyimide, parylene, benzocyclobutene (BCB), and fluoropolymers such as polytetrafluoroethylene (PTFE). Means for forming the additional layer are well known to those skilled in the art and include dip coating, spay coating, spin coating, chemical vapor deposition, plasma assisted vapor deposition and screen printing; the additional layer being formed following training of the SMA substrate and at a temperature below an activation temperature of the substrate. An activation temperature for an SMA actuator included in an interventional medical device must be sufficiently high to avoid accidental activation at body temperature; a temperature threshold consistent with this requirement and having a safety factor built in is approximately 60° C. This lower threshold of approximately 60° C. may also prevent accidental activation during shipping of the medical device. An activation temperature must also be sufficiently low to avoid thermal damage to body tissues and fluids; a maximum temperature consistent with this requirement is approximately 100° C., but will depend upon thermal insulation and, or cooling means employed in a medical device incorporating an SMA actuator.

FIG. 2B is a plan view of a portion of a surface of an SMA actuator 50. FIG. 2B illustrates a group of conductive trace patterns; portions of the conductive trace patterns are formed either on a first layer, a second layer, or between the first and second layer of a multi-layer electrical insulation 1 formed on a surface of an SMA substrate, such as strip 20 illustrated in FIG. 2A. As illustrated in FIG. 2B, conductive trace pattern includes heating element traces 2, which are formed on first layer of insulation 1, signal traces 4, 5, which are formed on second layer of insulation 1, and conductive vias 3, 9, which traverse second layer in order to electrically couple heating element signal traces 2 on first layer with signal traces 4, 5 on second layer. Each signal trace 4 extends from an interconnect pad 6 through via 3 to heating element trace 2, while signal trace 5 extends from all heating element traces 2 through vias 9 to a common interconnect pad 7. According to embodiments of the present invention, multi-layer insulation 1 is formed of an inorganic electrically insulative material, examples of which are presented above, deposited or formed directly on the SMA substrate. Portions of conductive trace pattern deposited upon each layer of multi-layer insulation 1, according to one embodiment, are formed of a first layer of titanium, a second layer of gold and a third layer of titanium and each interconnect pad 6, 7 is formed of gold deposited upon the second layer of insulation 1. Details regarding pattern designs, application processes, thicknesses, and materials of conductive traces that may be included in embodiments of the present invention are known to those skilled in the arts of VLSI and photolithography.

Figure 3:
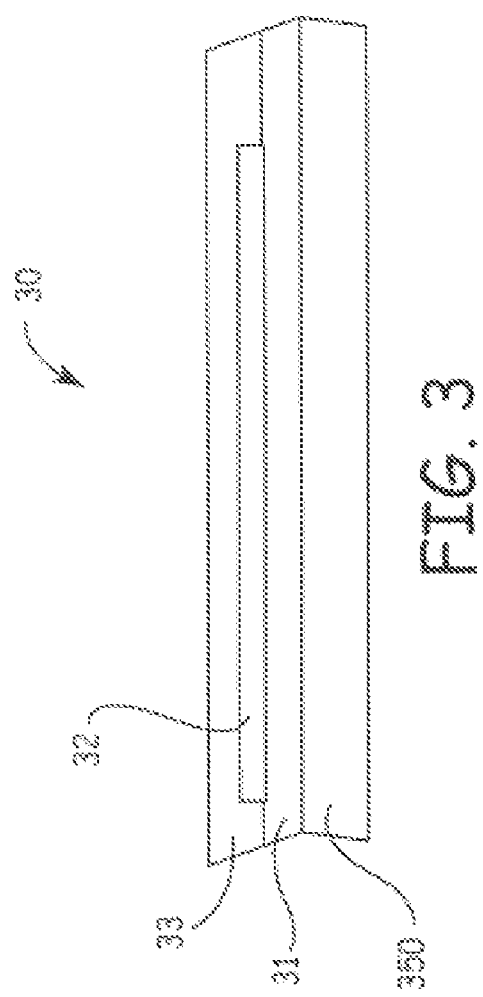
FIG. 3 is a section view through a portion of an SMA actuator according an embodiment of the present invention.
Figure 4:
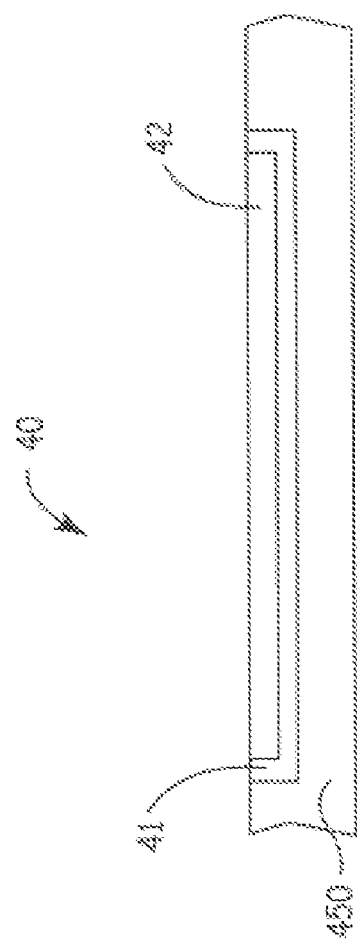
FIG. 4 is a section view through a portion of an SMA actuator according to an alternate embodiment of the present invention.

Section views in FIGS. 3 and 4 illustrate embodiments of the present invention in two basic forms. FIG. 3 is a section view through a portion of an SMA actuator 30 including one segment of a conductive trace 32 that may be a portion of a heating element trace, such as a heating element trace 2 illustrated in FIG. 2B. As illustrated in FIG. 3, SMA actuator 30 further includes an SMA substrate 350, a first insulative layer 31, electrically isolating conductive trace 32 from SMA substrate 350, and a second insulative layer 33 covering and surrounding conductive trace 32 to electrically isolate conductive trace 32 from additional conductive traces that may be included in a pattern, such as the pattern illustrated in FIG. 2B. According to embodiments of the present invention, first insulative layer 31, including an inorganic material, is deposited or formed directly on substrate 350, as described in conjunction with FIG. 2A. Conductive materials are deposited or applied on insulative layer 31, creating conductive trace 32, for example by etching, and then second insulative layer 33, including an inorganic material, is deposited or applied over conductive trace 32. In an alternate embodiment, second insulative layer 33 includes an organic electrically insulative material; examples of suitable organic materials include polyimide, parylene, benzocyclobutene (BCB), and fluoropolymers such as polytetrafluoroethylene (PTFE).

Means for forming insulative layer 33 include dip coating, spray coating, spin coating, chemical vapor deposition, plasma assisted vapor deposition and screen-printing. Training of SMA substrate 350 may follow or precede formation of first insulative layer 31, as previously described in conjunction with FIG. 2A.

FIG. 4 is a section view through a portion of an SMA actuator 40 including one segment of a conductive trace 42. According to alternate embodiments of the present invention, a groove in a surface of an SMA substrate 450 (reference FIG. 5A) establishes a pattern for conductive trace 42, the pattern including a heating element trace disposed between signal traces, similar to one of heating element traces 2 and corresponding signal traces 4, 5 illustrated in FIG. 2B. As illustrated in FIG. 4, an insulative layer 41 is disposed between conductive trace 42 and SMA substrate 450 electrically isolating conductive trace 42 from an SMA substrate 450. According to embodiments of the present invention, insulative layer 41 includes an inorganic material, examples of which are given in conjunction with FIG. 2A, formed directly on SMA substrate 450. Training of SMA substrate 450 may follow or precede formation of first insulative layer 41 including an inorganic material, as previously described in conjunction with FIG. 2A. According to alternate embodiments of the present invention, insulative layer 41 includes an organic material, formed directly on SMA substrate 450 following training of substrate 450. Selected organic materials for insulative layer 41 include those which may be deposited or applied at a temperature below an activation temperature of SMA substrate 450 and those which will not degrade at the activation temperature of SMA substrate 450; examples of such materials include polyimide, parylene, benzocyclobutene (BCB), and fluoropolymers such as polytetrafluoroethylene (PTFE). Means for forming insulative layer 41 include dip coating, spray coating, spin coating, chemical vapor deposition, plasma assisted vapor deposition and screen-printing.

Figure 5A:
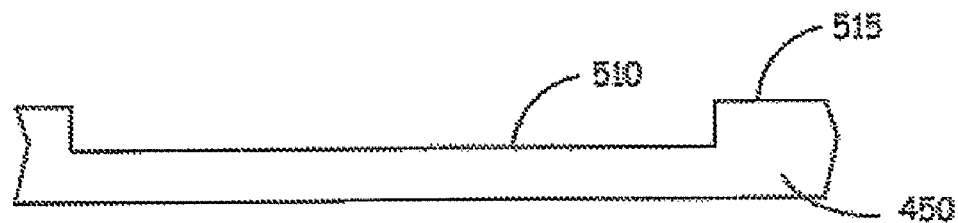
FIGS. 5A-D are section views illustrating steps, according to embodiments of the present invention, for forming the SMA actuator illustrated in FIG. 4.
Figure 5B:
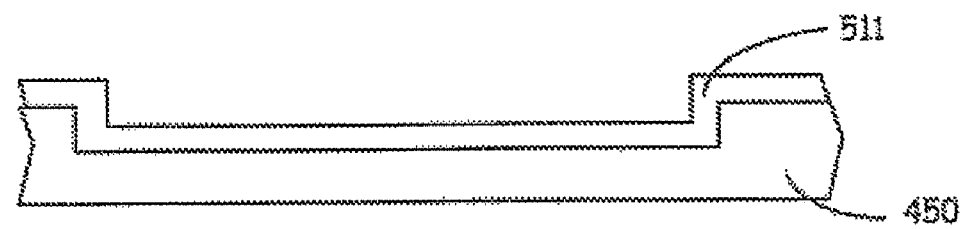
Figure 5C:
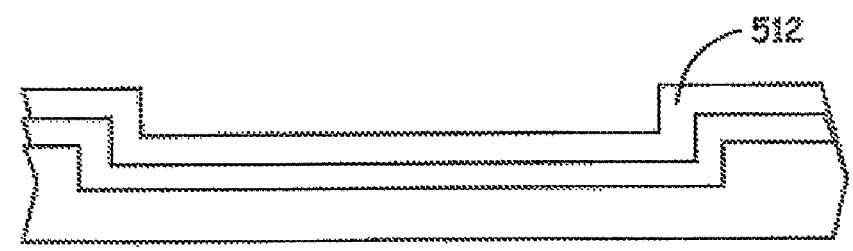
Figure 5D:
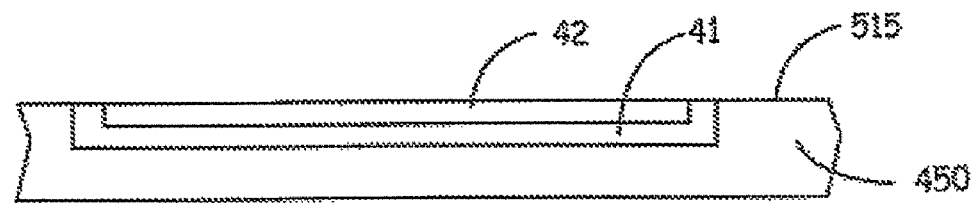

FIGS. 5A-D are section views illustrating steps, according to embodiments of the present invention, for forming SMA actuator 40 illustrated in FIG. 4. FIG. 5A illustrates SMA substrate 450 including a groove 510 formed in a surface 515; groove 510 is formed, for example by a machining process. FIG. 5B illustrates a layer of electrically insulative material 511 formed on surface 515 and within groove 510. FIG. 5C illustrates a layer of conductive material 512 formed over layer of insulative material 511. FIG. 5D illustrates insulative layer 41 and conductive trace 42 left in groove 510 after polishing excess insulative material 511 and conductive material 512 from surface 515. As illustrated in FIG. 5D, conductive trace 42 is flush with surface 515 following polishing; in one example, according to this embodiment, groove 510 is formed having a width of approximately 25 micrometer and a depth of approximately 1.2 micrometer approximately matching a predetermined combined thickness of insulative layer 41 and conductive trace 42. According to alternate embodiments of the present invention, groove 510 is formed deeper than a resultant combined thickness of the insulative layer 41 and conductive trace 42 so that conductive trace is recessed from surface 515.

EXAMPLES

Minimum theoretical thicknesses having sufficient dielectric strength for operating voltages of 100V, 10V, and 1V applied across conductive traces on SMA actuators were calculated for insulating layers of Silicon Nitride, Aluminum Nitride, Boron Nitride, and polyimide according to the following formula:

Thickness=voltage/dielectric strength.

A dielectric strength for Silicon Nitride was estimated to be 17700 volts/millimeter; a dielectric strength for Aluminum Nitride was estimated to be 15,000 volts/millimeter; a dielectric strength for Boron Nitride was estimated to be 3,750 volts/millimeter; a dielectric strength for polyimide was estimated to be 157,500 volts/millimeter. Results are presented in Table 1.

TABLE 1

|  | Thickness, 100 V (micrometer) | Thickness, 10 V (micrometer) | Thickness, 1 V (micrometer) |
| --- | --- | --- | --- |
| Silicone Nitride | 5.65 | 0.56 | 0.06 |
| Aluminum Nitride | 6.67 | 0.67 | 0.07 |
| Boron Nitride | 26.7 | 2.67 | 0.27 |
| Polyimide | 0.64 | 0.064 | 0.0064 |

Finally, it will be appreciated by those skilled in the art that numerous alternative forms of SMA substrates and trace patterns included in SMA actuators and employed in medical devices are within the spirit of the present invention. For example, SMA actuators according to the present invention can include conductive trace patterns on two or more surfaces of an SMA substrate or an additional layer or layers of non-SMA material joined to an SMA substrate, which serve to enhance biocompatibility or radiopacity in a medical device application. Hence, descriptions of particular embodiments provided herein are intended as exemplary, not limiting, with regard to the following claims.

The invention claimed is:

1. An elongated medical device adapted for controlled deformation by means of one or more actuators, the one or more actuators comprising:
   a shape memory alloy (SMA) substrate including a surface, a groove being defined in the surface of the SMA substrate establishing a trace pattern;
   an electrically insulative layer formed within the groove;
   a conductive trace formed upon the electrically insulative layer within the groove and electrically isolated from the SMA substrate by the electrically insulative layer formed within the groove, the conductive trace including a first end, a second end, and a heating element disposed between the first end and the second end, wherein at least portions of the conductive trace, portions of the electrically insulative layer electrically isolating the conductive trace from the SMA substrate within the groove, and portions of the SMA substrate are flush after the conductive trace has been formed upon the electrically insulative layer within the groove;
   a first interconnect pad terminating the first end of the trace; and
   a second interconnect pad terminating the second end of the trace;
   wherein the SMA substrate is trained to deform at a transition temperature achieved when electricity is conducted through the conductive trace via the first and second interconnect pads.

2. The medical device of claim 1, wherein the insulative layer comprises an organic material.

3. The medical device of claim 2, wherein the organic material is a polyimide.

4. The medical device of claim 2, wherein the organic material comprises a fluoropolymer.

5. The medical device of claim 2, wherein the organic material comprises parylene.

6. The medical device of claim 2, wherein the organic material comprises benzocyclobutene.

7. The medical device of claim 1, wherein a thickness of the electrically insulative layer over which the conductive trace is formed is between approximately 0.5 micrometer and approximately 1 micrometer.

8. The medical device of claim 1, wherein a thickness of the electrically insulative layer over which the conductive trace is formed is less than approximately 0.5 micrometer.

9. The medical device of claim 1, wherein a dielectric strength of the electrically insulative layer over which the conductive trace is formed is functionally sufficient for an applied operating voltage greater than approximately 100V.

10. The medical device of claim 1, wherein a dielectric strength of the electrically insulative layer over which the conductive trace is formed is functionally sufficient for an applied operating voltage greater than approximately 10V.

11. The medical device of claim 1, wherein a dielectric strength of the electrically insulative layer over which the conductive trace is formed is functionally sufficient for an applied operating voltage between approximately 1V and approximately 10V.

12. The medical device of claim 1, wherein the insulative layer comprises a composite of an inorganic material and an organic material wherein the organic material is selected from the group consisting of fluoropolymer, parylene, and benzocyclobutene.

13. The medical device of claim 12, wherein the inorganic material is selected from a group consisting of oxides, nitrides, and carbides.

14. A shape memory alloy (SMA) actuator comprising:
an SMA substrate including a surface, a groove being defined in the surface of the SMA substrate establishing a trace pattern;
an electrically insulative layer formed within the groove;
a conductive trace formed upon the electrically insulative layer within the groove and electrically isolated from the SMA substrate by the electrically insulative layer formed within the groove, the trace including a first end, a second end, and a heating element disposed between the first end and the second end, wherein at least portions of the conductive trace, portions of the electrically insulative layer electrically isolating the conductive trace from the SMA substrate within the groove, and portions of the SMA substrate are flush after the conductive trace has been formed upon the electrically insulative layer within the groove;
a first interconnect pad terminating the first end of the trace; and
a second interconnect pad terminating the second end of the trace;
wherein the SMA substrate is trained to deform at a transition temperature achieved when electricity is conducted through the conductive trace via the first and second interconnect pads.

15. The SMA actuator of claim 14, wherein the insulative layer comprises an organic material.

16. The SMA actuator of claim 15, wherein the organic material is polyimide.

17. The SMA actuator of claim 15, wherein the insulative layer comprises a fluoropolymer.

18. The SMA actuator of claim 15, wherein the organic material comprises parylene.

19. The SMA actuator of claim 15, wherein the organic material comprises benzocyclobutene.

20. The SMA actuator of claim 14, wherein a thickness of the electrically insulative layer over which the conductive trace is formed is between approximately 0.5 micrometer and approximately 1 micrometer.

21. The SMA actuator of claim 14, wherein the insulative layer comprises a composite of an inorganic material and an organic material being one of fluoropolymer, parylene, and benzocyclobutene.

22. The SMA actuator of claim 21, wherein the inorganic material is selected from a group consisting of oxides, nitrides, and carbides.

23. The SMA actuator of claim 14, wherein a thickness of the electrically insulative layer over which the conductive trace is formed is less than approximately 0.5 micrometer.

24. The SMA actuator of claim 14, wherein a dielectric strength of the electrically insulative layer over which the conductive trace is formed is functionally sufficient for an applied operating voltage greater than approximately 100V.

25. The SMA actuator of claim 14, wherein a dielectric strength of the electrically insulative layer over which the conductive trace is formed is functionally sufficient for an applied operating voltage greater than approximately 10V.

26. The SMA actuator of claim 14, wherein a dielectric strength of the electrically insulative layer over which the conductive trace is formed is functionally sufficient for an applied operating voltage between approximately 1V and approximately 10V.

27. An elongated medical device adapted for controlled deformation by means of one or more actuators, the one or more actuators comprising:
a shape memory alloy (SMA) substrate including a surface, a groove being defined in the surface of the SMA substrate establishing a trace pattern;
an electrically insulative layer formed within the groove;
a conductive trace formed upon the electrically insulative layer within the groove and electrically isolated from the SMA substrate by the electrically insulative layer formed within the groove, the trace including a first end, a second end, and a heating element disposed between the first end and the second end, wherein at least portions of the conductive trace, portions of the electrically insulative layer electrically isolating the conductive trace from the SMA substrate within the groove, and portions of the SMA substrate are flush after the conductive trace has been formed upon the electrically insulative layer within the groove;
a first interconnect pad terminating the first end of the trace; and
a second interconnect pad terminating the second end of the trace;
wherein the SMA substrate is trained to deform at a transition temperature, the transition temperature being achieved when electricity is conducted through the conductive trace via the first and second interconnect pads, and
wherein the insulative layer comprises a composite of an inorganic material and an organic material.

28. The elongated medical device of claim 27, wherein the composite comprises a first layer comprising the inorganic material and a second layer comprising the organic material.

* * * * *